June 29, 1937. J. H. NICOLAS Plant Pat. 253
ROSE
Filed Feb. 11, 1937
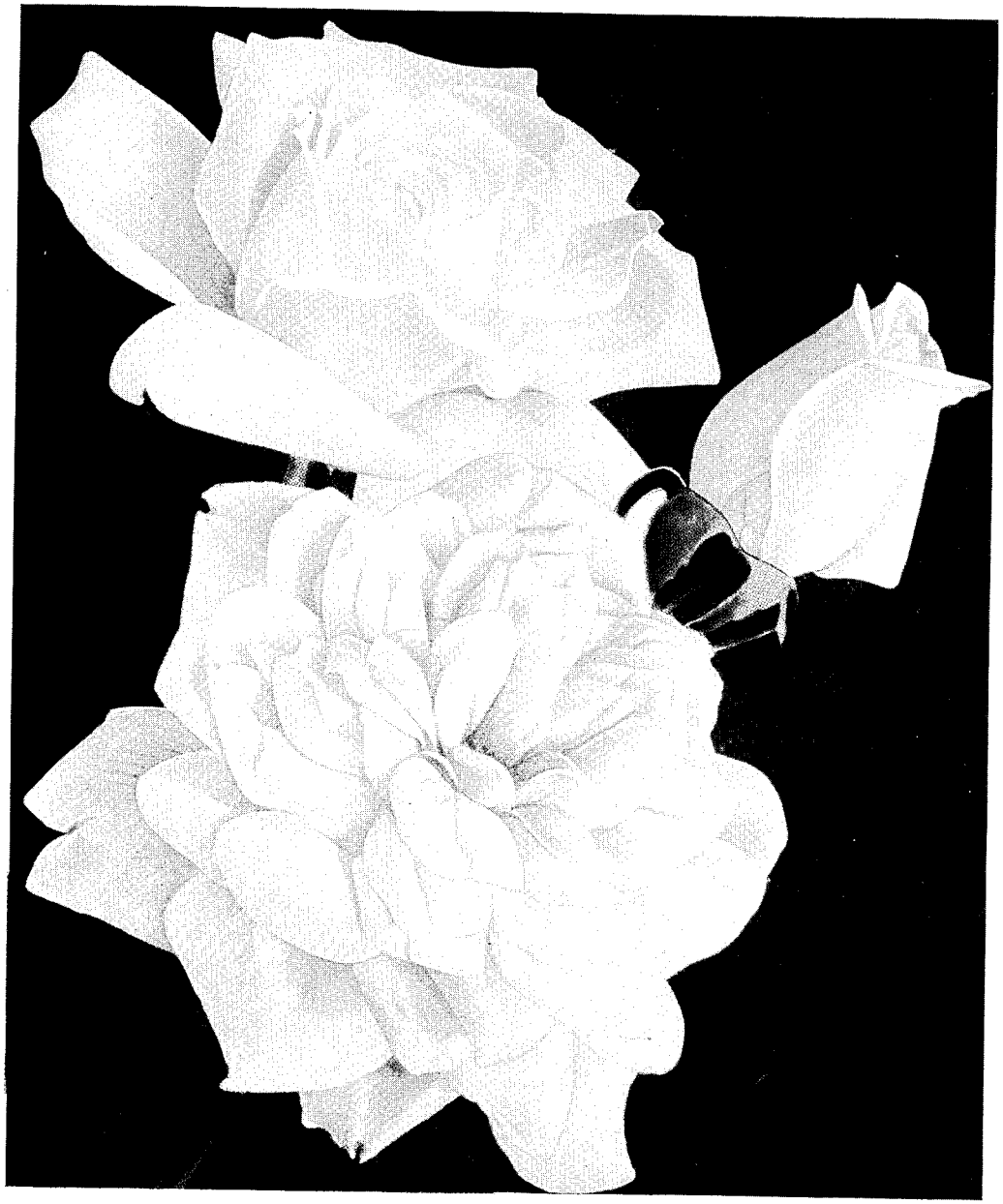
Inventor
J. H. Nicolas
By Robb & Robb
attorneys Patented June 29, 1937

Plant Pat. 253

UNITED STATES PATENT OFFICE

253

ROSE

Jean H. Nicolas, Newark, N. Y., assignor to Jackson & Perkins Company, Newark, N. Y.

Application February 11, 1937, Serial No. 125,330

1 Claim. (Cl. 47—61)

This invention relates to a new and distinct variety of rose plant, the result of a definite effort to perpetuate a new hardy strain, originated by me, with large flowers, great floribundity and vigorous constitution.

Of this new strain referred to, the variety "Leonard Barron" was first to be disseminated, this being the first ever-blooming garden rose evolved from R. Nutkana of Alaska. Its genealogy is (R. Nutkana X Paul Neyron) X Souvenir de Mme. Boullet, a yellow hybrid tea, but due to the fact that it is nearly sterile as a female, it was not used as the seed bearer for the origination of the present variety. However, I found that the pollen of Leonard Barron is very potent and capable of reproducing its plant characters which I desired to breed into the new rose.

Therefore, the present invention was produced by crossing Leonard Barron as pollen parent with "Lady Lilford", a yellow sport of the Pernetiana "Independence Day", noted for its floriferousness and its good seed bearing characteristics.

As the objective result of this cross, I have produced a new type of white rose, having the characteristics first above given as to size and floriferousness and vigor. From tests made under various climatic conditions in different parts of the country, this new rose is susceptible of being used in a much larger climatic range than any rose of the hybrid tea class, its performance being uniform in the north as well as in the south.

The new rose has been reproduced by budding and has always come true to type.

The following is a detailed description of the new variety, color designations according with the Gravereaux color chart except where obviously the ordinary dictionary definition is intended:—

Parentage:
Seedling:
*Seed parent.*—Lady Lilford (yellow sport of "Independence Day").
*Pollen parent.*—Leonard Barron.
Classification:
*Botanic.*—Hybrid of R. Nutkana.
*Commercial.*—Hybrid Tea.

*Flower*

Blooming habit:
Location where observations were made Jackson & Perkins Co. Nurseries, Newark, N. Y.
*Recurrent.*—Continuous.
Bud:
*Size.*—Very large.
*Form.*—Pointed.
Unaffected by wet or hot weather.
*Color.*—When sepals first divide—ivory. When petals begin to unfurl—ivory, white edges. When half blown—inside of petals—bottom ivory, edges white; reverse of petals—base ivory, edges white.
*Sepals.*—Branched, curl back as bud unfurls.
*Calyx.*—Shape—funnel. Size—broad. Aspect—smooth. No odor when rubbed.
*Peduncle.*—Length—very long. Aspect—smooth. Color—medium green. Strength—erect, heavy.
*Opening.*—Bud opens well.
Is not affected by adverse conditions.
Bloom:
*Size.*—Very large, up to 5″ when fully expanded.
*Borne.*—Singly.
*Stems.*—Long, strong.
*Form.*—When first open—high center, globular.
*Permanence.*—flattens.
*Petalage.*—Very double (many petals and stamens hidden).
75 to 100 petals under normal conditions.
*Color.*—Center of flower—ivory. Outer petals—White. Base of petals (aiglet)—ivory. Inside and reverse of petals—base ivory, edges white. General tonality from a distance—ivory white.
*Variegations.*—None.
*Discoloration.*—General tonality at end of first and second days—ivory. Third day—white.
Petals:
*Texture.*—Thick.
Unaffected by wet or hot weather.
*Appearance.*—Inside and outside, satiny.
*Form.*—Round.
*Arrangement.*—Imbricated (regularly arranged shinglelike). Petaloids in center—few, small.
*Persistence.*—Hang on and dry.
*Fragrance.*—Moderate. Nature—sweet briar.
*Lasting quality.*—On the plant and as cut flower—very long.
Genital organs:
*Stamens, anthers.*—Medium size, few. Color—yellow. Arrangement—mixed with petaloids.
*Stamens, filaments (threads).*—Medium. Color—white.
*Pollen.*—Lemon yellow.
*Styles.*—Uneven length, medium length, heavy.
*Stigmas.*—White.
*Ovaries.*—Some protruding from calyx.
Fruit:
Variety is fertile with its own pollen.
*Form.*—Round, depressed top.
*Aspect.*—Smooth.
*Color at maturity.*—Russet brown.
*Sepals.*—Caducous (soon falling).

*Plant*

Form:
Bush.
Growth:
Very vigorous.
Foliage:
Generally five leaflets, sometimes 7.
*Size.*—Medium.

*Quantity.*—Abundant.

*Color.*—New foliage, upper side—dark green; under side—lighter green. Old foliage, upper side—dark green; under side—lighter green.

*Shape.*—Oval pointed.

*Texture.*—Upper side—glossy. Under side—rough. Ribs and veins—prominent.

*Edge.*—Serrated (saw toothed).

*Serration.*—Single, large.

*Rachis.*—Color—green. Under side—prickles.

*Stipules.*—Medium, smooth.

*Disease resistance.*—Susceptible to mildew.

Wood:

*New wood.*—Color—light green. Bark—smooth.

*Old wood.*—Color—green. Bark—smooth.

Thorns: (Divided into thorns, prickles and short needles)

*Thorns.*—Quantity—on main stalks from base—ordinary; on laterals from stalk—few. Form—broad base, medium, hooked downward. Color when young—green and red. Position—irregular.

*Prickles.*—Quantity—on main stalks—few; on laterals—few. Color—brown.

*Short needles.*—Quantity—none.

I claim:

A new and distinct variety of white rose, characterized by its vigorous constitution, its uniform performance under various climatic conditions, thereby enlarging its climatic range beyond that of any known rose of the Hybrid Tea class, its large size flowers and great floribundity, substantially as shown and described.

JEAN H. NICOLAS.